United States Patent
Allier et al.

(10) Patent No.: US 9,970,858 B2
(45) Date of Patent: May 15, 2018

(54) METHOD AND SYSTEM FOR DETECTING AT LEAST ONE PARTICLE IN A BODILY FLUID, AND ASSOCIATED METHOD FOR DIAGNOSING MENINGITIS

(71) Applicant: COMMISSARIAT A L'ENERGIE ATOMIQUE ET AUX ENERGIES ALTERNATIVES, Paris (FR)

(72) Inventors: Cedric Allier, Grenoble (FR); Michel Drancourt, Marseilles (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 13 days.

(21) Appl. No.: 15/307,539

(22) PCT Filed: Apr. 29, 2015

(86) PCT No.: PCT/EP2015/059423
§ 371 (c)(1),
(2) Date: Oct. 28, 2016

(87) PCT Pub. No.: WO2015/166009
PCT Pub. Date: Nov. 5, 2015

(65) Prior Publication Data
US 2017/0045439 A1 Feb. 16, 2017

(30) Foreign Application Priority Data
Apr. 30, 2014 (FR) ..................... 14 53959

(51) Int. Cl.
*G01N 15/00* (2006.01)
*G01N 15/14* (2006.01)
*G03H 1/04* (2006.01)

(52) U.S. Cl.
CPC ....... *G01N 15/1475* (2013.01); *G03H 1/0443* (2013.01); *G01N 2015/008* (2013.01);
(Continued)

(58) Field of Classification Search
CPC ...... G02B 21/32; G02B 27/1086; G02B 5/32; G02B 5/18; G02B 27/42; G02B 27/4244;
(Continued)

(56) References Cited

U.S. PATENT DOCUMENTS 9,767,341 B2 * 9/2017 Ozcan ................ G06K 9/00127
2013/0274119 A1 * 10/2013 Knutson ............ G01N 15/0211
506/9
(Continued)

FOREIGN PATENT DOCUMENTS

EP  2 602 608 A1  6/2013
EP  2 669 678 A1  12/2013
(Continued)

OTHER PUBLICATIONS

Hand, A. J., et al.: "Automated tracking of migrating cells in phase-contrast video microscopy sequences using image registration", Apr. 1, 2009 (Apr. 1, 2009), Journal of Microscopy, vol. 234, pp. 62-79, XP055158603, DOI: 10.1111/j.1365-2818.2009.03144.x, Retrieved from the Internet: URL: :http://onlinelibrary.wiley.com/doi/10.1111/j.1365-28182009.03144.x/pdf.
(Continued)

*Primary Examiner* — Michael P Stafira
(74) *Attorney, Agent, or Firm* — Young & Thompson (57) ABSTRACT

This method for detecting at least one particle in a bodily fluid is carried out via a detection system including a light source, a transparent substrate and a photodetector array, the substrate being positioned between the light source and the photodetector. This method includes the placement of a droplet of bodily fluid on the substrate, the illumination of
(Continued)

the droplet via the light source, the acquisition of several successive images of the droplet via the photodetector, each image being formed by radiation transmitted by the illuminated droplet and including at least one elementary diffraction pattern, each elementary diffraction pattern corresponding to waves diffracted by a particle upon illumination of the droplet, the identification, via the acquired images of the mobile elementary diffraction patterns, and the counting of moving particles in the droplet, via the identified mobile elementary diffraction patterns.

12 Claims, 6 Drawing Sheets

(52) U.S. Cl.
CPC ............... *G01N 2015/0065* (2013.01); *G01N 2015/144* (2013.01); *G01N 2015/1454* (2013.01); *G01N 2015/1481* (2013.01); *G01N 2015/1486* (2013.01); *G03H 2001/0447* (2013.01)

(58) Field of Classification Search
CPC .. G02B 27/425; G02B 27/283; G02B 5/1833; G02B 5/3016; G02B 26/001; G02B 27/1093; G02B 5/1861; G02B 5/201; G02B 5/28

See application file for complete search history.

(56) References Cited

U.S. PATENT DOCUMENTS

| | | | |
|---|---|---|---|
| 2016/0299158 A1 | 10/2016 | Poher et al. | |
| 2017/0317125 A1* | 11/2017 | Bordy | ............... H01L 27/14625 |
| 2017/0356846 A1* | 12/2017 | Genuer | ................ G01N 21/474 |

FOREIGN PATENT DOCUMENTS

| | | |
|---|---|---|
| WO | 2011/049965 A1 | 4/2011 |
| WO | 2014/012031 A1 | 1/2014 |

OTHER PUBLICATIONS

French Preliminary Search Report, dated Dec. 17, 2014, from corresponding French Application.
International Search Report, dated Jul. 7, 2015, from corresponding PCT Application.

* cited by examiner

METHOD AND SYSTEM FOR DETECTING AT LEAST ONE PARTICLE IN A BODILY FLUID, AND ASSOCIATED METHOD FOR DIAGNOSING MENINGITIS

FIELD OF THE INVENTION

This detection method is applied with a detection system comprising a light source, a transparent substrate and a photodetector array, the transparent substrate being positioned between the light source and the photodetector array.

The invention also relates to a method for diagnosing meningitis, comprising the determination of a number of white corpuscles in a predetermined amount of cerebrospinal liquid with such a detection method, the bodily fluid being the cerebrospinal liquid and the detected particles being the white corpuscles contained in said cerebrospinal liquid. The meningitis is then diagnosed if the number of detected white corpuscles in the predetermined amount of cerebrospinal liquid is greater than a predetermined threshold value.

The invention also relates to a system for detecting at least one particle in the bodily fluid.

The invention generally relates to the detection of particles, such as cells, in a bodily fluid, this notably in order to detect as early as possible a possible disease. The detection of white corpuscles in the cerebrospinal liquid for example allows diagnostic of meningitis cases.

BACKGROUND OF THE INVENTION

An experimental procedure known for detecting white corpuscles in the cerebrospinal liquid then consists of depositing, on a microscope slide, a droplet of about 10 µL of cerebrospinal liquid which has been sampled beforehand on the patient, the sampling step not being concerned by the present invention.

It is agreed that meningitis is diagnosed if a 10 µl sample of cerebrospinal liquid contains at least 10 white corpuscles, these white corpuscles being the indirect marking of a viral or bacterial infection.

However, the counting of these white corpuscles is a tedious operation for the technician and quite inaccurate, since the question is to count white corpuscles with a microscope. A more specific alternative, but much more expensive, long to be applied and requiring a cumbersome apparatus, consists of resorting to cytometry methods.

SUMMARY OF THE INVENTION

The object of the invention is therefore to propose a method and a system for detecting particles in the bodily fluid which is less expensive and easier to apply. From an experimental point of view, the invention then gives the possibility of carrying out continuous counting of the detected particles, and if necessary diagnosing a particular disease.

For this purpose, the subject-matter of the invention is a method for detecting at least one particle in a bodily fluid, with a detection system comprising a light source, a transparent substrate and a photodetector array, the transparent substrate being positioned between the light source and the photodetector array, the method comprising the following steps:
  placing the bodily fluid as a droplet on the transparent substrate,
  illuminating the droplet with the light source,
  acquiring several successive images of the droplet with the photodetector array, each image being formed by radiation transmitted by the illuminated droplet and including at least one elementary diffraction pattern, each elementary diffraction pattern corresponding to waves diffracted by a particle during the illumination of the droplet,
  identifying, from the acquired images, mobile elementary diffraction patterns, and
  counting the moving particles within the droplet, from the thereby identified mobile elementary diffraction patterns.

According to other advantageous aspects of the invention, the detection method comprises one or several of the following features, taken individually or according to all the technically possible combinations:
  the method further comprises a step for heating the droplet in order to promote displacement of particles within the droplet;
  each acquired image includes a plurality of pixels and the photodetector array is adapted for measuring the intensity of each pixel, and the step for identifying the mobile elementary diffraction patterns includes:
    the determination, for each pixel of the image, of the median value or of the average intensity value of said pixel for a set of acquired images,
    computing, for at least one acquired image, an image resulting by substraction, for each pixel of the acquired image, of said median value or said average value, and
    detecting, on each resulting image, at least one diffraction pattern, each detected diffraction pattern on the resulting image corresponding to a mobile elementary diffraction pattern;
  the identification step further includes the tracking of each detected elementary diffraction pattern from one resulting image to the following resulting image, each mobile elementary diffraction pattern having, between two successive resulting images, a displacement greater than a predetermined minimum distance;
  the step for identifying the mobile elementary diffraction patterns includes:
    detection, on each acquired image, of at least one elementary diffraction pattern corresponding to a particle within the droplet, and
    tracking each detected elementary diffraction pattern from an acquired image to the next acquired image, each mobile elementary diffraction pattern having, between two successive acquired images, a displacement greater than a predetermined minimum distance;
  the method further comprises a step for characterization of the detected moving elementary diffraction patterns and a step for classifying the patterns characterized according to at least two distinct categories;
  the characterization step includes the computation, for each identified mobile elementary diffraction pattern, of a ratio between the maximum intensity and the median intensity of a region of interest of the image including said identified mobile elementary diffraction pattern, the classification of said diffraction pattern then being carried out depending on the value of the computed ratio;
  the detection step includes the localization in the image of the center of each elementary diffraction pattern;

the localization in the image of the center of each elementary diffraction pattern is carried out via autocorrelation with a reference elementary diffraction pattern;

the localization in the image of the center of each elementary diffraction pattern is achieved from:

reconstruction of an image of the particle associated with said elementary diffraction pattern, by applying a reconstruction algorithm, and then detecting, in the reconstructed image, the position corresponding to the center of said elementary diffraction pattern.

The subject-matter of the invention is also a method for diagnosing meningitis comprising the following steps:

determining a number of white corpuscles in a predetermined amount of cerebrospinal liquid with a detection method as defined above, the bodily fluid being the cerebrospinal liquid and the detected particles being the white corpuscles contained in said cerebrospinal liquid, and diagnosing meningitis if the number of white corpuscles in the predetermined amount of cerebrospinal liquid is greater than a predetermined threshold value.

The subject-matter of the invention is also a system for detecting at least one particle in a bodily fluid, the system comprising:

a transparent substrate adapted for receiving the bodily fluid as a droplet, a light source adapted for emitting a light beam for illuminating the droplet, a photodetector array adapted for acquiring several successive images of the droplet, each image being formed by radiation transmitted by the illuminated droplet and including at least one elementary diffraction pattern, each elementary diffraction pattern corresponding to waves diffracted by a particle during the illumination of the droplet, and an information processing unit adapted for:

identifying, from acquired images, mobile elementary diffraction patterns, counting the moving particles within the droplet, from the identified mobile elementary diffraction patterns.

BRIEF DESCRIPTION OF THE DRAWINGS

The features and advantages of the invention will become apparent upon reading the description which follows, only given as a non-limiting example, and made with reference to the appended drawings, wherein.

DETAILED DESCRIPTION OF THE PREFERRED EMBODIMENTS

In the following of the description, the expression <<substantially equal to>> defines an equality relationship to within more or less 5%.

Figure 1:
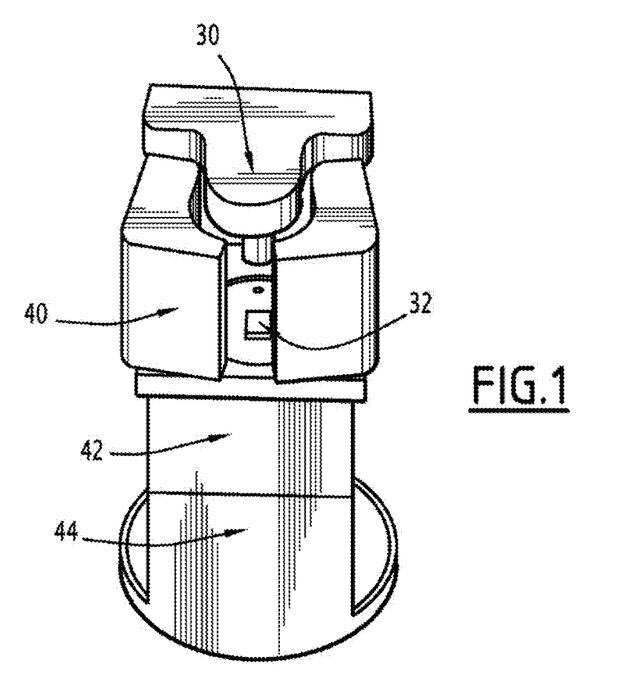
FIG. 1 is a perspective view of a detection system according to the invention.
Figure 2:
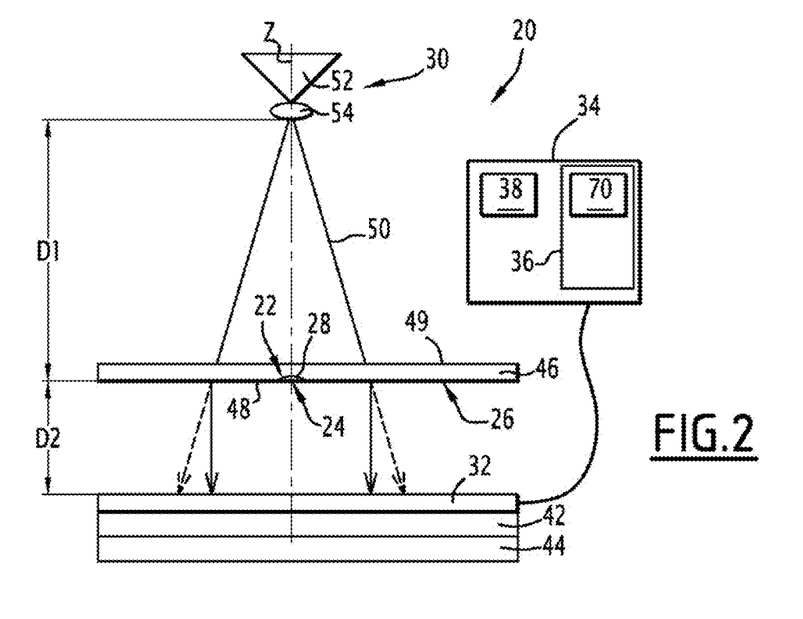
FIG. 2 is a schematic illustration of the detection system of FIG. 1, the detection system comprising a light source, a transparent substrate adapted for receiving the bodily fluid as a droplet, a photodetector array adapted for acquiring successive images of the droplet and an information processing unit, the information processing unit being configured for identifying, from acquired images, mobile elementary diffraction patterns, and then for counting the moving particles within the droplet, from the identified mobile elementary diffraction patterns.

In FIGS. 1 and 2, a system 20 for detecting particles 22 contained in a bodily fluid 24, comprises a transparent substrate 26 adapted for receiving the bodily fluid 24 as a droplet 28. The detection system 20 also comprises a light source 30 and a photodetector array 32 adapted for acquiring several successive images of radiation transmitted by the droplet 28 illuminated by the light source 30.

The detection system 20 is generally adapted for detecting the particles 22 in the bodily fluid 24 via a methodology by imaging without any lens, the photodetector array 32 not including any magnification optics.

The detection system 20 also comprises an information processing unit 34, visible in FIG. 2, including a memory 36 and a processor 38 associated with the memory 36.

As an optional addition, the detection system 20 comprises a device 40 with swinging doors, the doors being painted in black, giving the possibility of isolating the radiation transmitted by the illuminated droplet 28 from the external environment. The device with swinging doors 40 when the swinging doors are shut, allows the technician to then operate in ambient light, without however perturbing the measurements conducted inside the detection system.

The detection system 20 also comprises a heat dissipater 42 and a fan 44 for regulating the temperature of the photodetector array 32, notably for cooling it in the case of too intense heating. These elements are optional.

The diffracting particles 22 are for example biological particles, i.e. cells (notably blood cells and for example white corpuscles, also called white blood cells, or red, also called red blood cells), bacteria or bacterial colonies, or further cell aggregates.

The diffracting particles 22 generally have a diameter of less than 100 µm. The diameter of the diffracting particles 22 is for example comprised between 1 µm and 100 µm. The cells, such as the white corpuscles and the red corpuscles, have a diameter of the order of 10 µm.

The bodily fluid 24 is a fluid having been sampled beforehand on a patient, the sampling step not being part of the perimeter of the invention. The bodily fluid 24 is for example cerebrospinal liquid when the detection system 20 aims at diagnosing meningitis.

The transparent substrate 26 is positioned between the light source 30 and the photodetector array 32, and is substantially perpendicular to a vertical direction Z corresponding to the illumination direction of the bodily fluid 24 by the light source 30, as illustrated in FIG. 2.

The transparent substrate 26 for example comprises a transparent slide 48. In this example, the transparent substrate 26 is deposited at the bottom of a Petri dish 46. The transparent slide 48, made in a material such as glass, is used for controlling a wetting angle of the droplet 28 so that the latter is not spread out too much, in order to facilitate its observation by imaging without any lens as a whole. The wetting angle, also called a contact angle, corresponds to the angle between the transparent slide 48 and the concave surface of the droplet 28 in the outer periphery of the droplet. Preferably, the wetting angle of the droplet is less than 90°, and still preferably substantially comprised between 30° and 60°. The Petri dish 46 here has a function for confining the bodily fluid 24, in order to protect the outer medium from the fluid. It is optional. It is adapted so as to be directly deposited on the photodetector array 32. The Petri dish 46 additionally includes a lid 49 in order to protect the bodily fluid 24.

The droplet 28 for example has a volume substantially equal to 10 µL, such a volume being generally used for a cerebrospinal liquid sample in the case of diagnosing meningitis.

The light source 30 is adapted for emitting a light beam 50 along the vertical direction Z in order to illuminate the bodily fluid 24 including the diffracting particles 22.

The light source 30 is positioned at a first distance D1 from the transparent slide 48 along the vertical direction Z. The first distance D1 preferably has a value comprised between 1 cm and 30 cm, for example equal to 5 cm.

The light source 30 is preferably spatially coherent and preferably monochromatic. The term of monochromatic designates a spectral width of less than 80 nm, preferably less than 50 nm at half-height.

The light source 30 for example includes a point-like source such as a light emitting diode 52, also called a LED (Light Emitting Diode), and a diaphragm 54 positioned in contact with the LED 52, as schematically illustrated in FIG. 2. The diaphragm 54 has a diameter comprised between 50 µm and 500 µm, preferably substantially equal to 150 µm. This gives the possibility of increasing the spatial coherence of the light radiation. The LED 52 for example has a wavelength substantially equal to 617 nm.

Alternatively, the light source 30 consists of the light emitting diode 52 and does not include any diaphragm. The light emitting diode 52 then has sufficiently reduced dimensions so as to be considered as spatially coherent, the diameter of the light emitting diode 52 then being for example less than one-tenth of the first distance D1.

Still alternatively, the light source 30 is a source of spatially and temporally coherent light, for example a laser diode laser or further a laser diode of the VCSEL (Vertical Cavity Surface Emitting Laser) type.

The photodetector array 32 is adapted for acquiring successive images of the radiation transmitted by the bodily fluid 24 as a droplet 28 containing the diffracting particles 22, illuminated by the light beam 50. By transmitted radiation is meant the radiation crossing the bodily fluid 24 so that the photodetector array 32 and the light source 30 are located on either side of the bodily fluid 24 including the diffracting particles 22.

The photodetector matrix 32 is a two-dimensional image sensor, i.e. in a plane substantially perpendicular to the vertical axis Z. The photodetector array 32 is a pixelized image sensor, for example a CMOS (Complementary Metal Oxide Semiconductor) sensor. Alternatively, the photodetector array 28 is a CCD (Charge Coupled Device) sensor.

The photodetector array 32 includes a plurality of pixels, not shown, each having dimensions smaller than or equal to 10 µm. In the example of FIGS. 1 and 2, each pixel has the shape of a square with a side substantially equal to 2.2 µm.

The photodetector array 32 may additionally include microlenses, not shown, each microlens being available above a corresponding pixel. Such microlenses are integrated to the sensor and give the possibility of improving the collection yield, without however forming magnification optics positioned between the transparent substrate 26 and the photodetector 32.

The images acquired by the photodetector array 32 are formed by the radiation directly transmitted by the illuminated bodily fluid 24, in the absence of any magnification optics positioned between the transparent substrate 26 and the photodetector array 32. The photodetector 32 is also called an imaging device without any lenses, and is capable of forming an image of the liquid 24, while being placed at a small distance from the latter. By small distance, is meant a distance of less than a few centimeters, preferably less than 1 cm. The photodetector 32 is positioned at a second distance D2 from the transparent slide 48 along the vertical direction Z, and the second distance D2 is then less than a few centimeters, preferably less than 1 cm, and for example equal to 700 µm.

By giving preference to a small value for the second distance D2, i.e. a small distance between the photodetector array 30 and the transparent substrate 26, gives the possibility of limiting the interference phenomena between various diffraction patterns when the bodily fluid 24 is illuminated.

Figure 4:
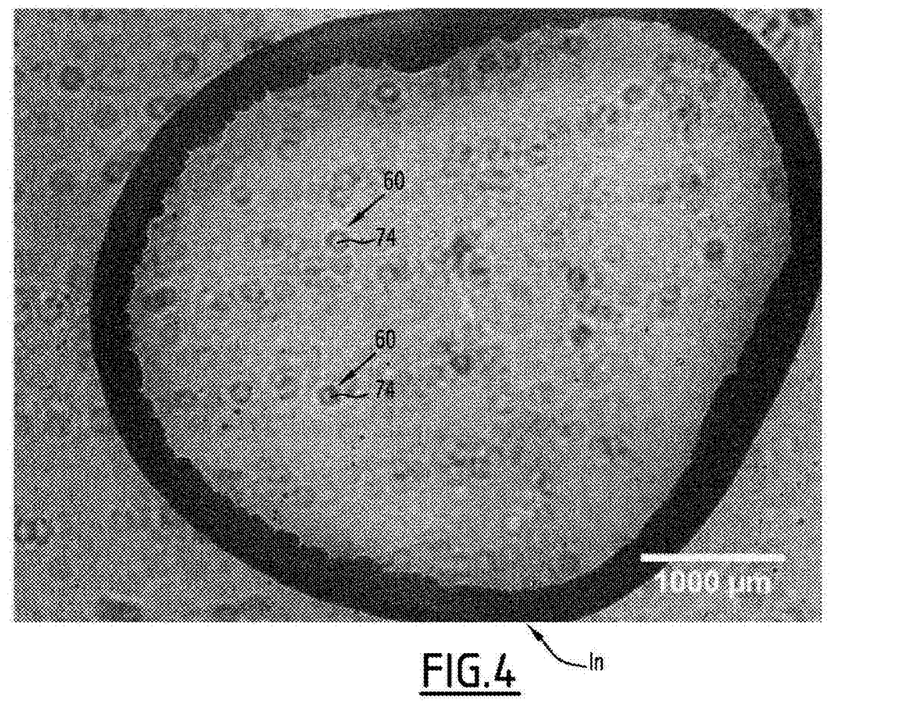
FIG. 4 is a view of an image acquired with the photodetector of FIG. 2, during the illumination of a droplet of cerebrospinal liquid.

The photodetector array 32 is then able to produce an image at least one elementary diffraction pattern 60 transmitted by the bodily fluid 24, each elementary diffraction pattern 60 corresponding to waves diffracted by a diffracting particle 22, during the illumination of the bodily fluid 24 as a droplet 28. Thus, the photodetector array 32 gives the possibility of obtaining an image $I_n$, said observed image including one or several elementary diffraction patterns 60, wherein n is an index comprised between 1 and N and corresponding to the number of the image in the acquired successive image sequence, with n and N being integers greater than or equal to 1. The acquisition rate is generally comprised between 50 images per second and one image every 10 to 20 seconds. FIG. 4 illustrates a plurality of elementary diffraction patterns 60 corresponding to white corpuscles, each pattern being formed with a central area, of which the intensity is substantially homogeneous, this central area being surrounded by concentric rings, the intensity of which is alternately low (dark rings) and high intensity (bright rings).

Each acquired image $I_n$ by the photodetector array 32 includes a plurality of pixels $I_n(x,y)$, each being localized by an abscissa x and an ordinate y in the image and the photodetector array 32 is adapted for measuring the intensity $I(x,y)$ of each pixel.

The memory 36 is able to store a software 70 for detecting particles 22 in the bodily fluid 24.

The processor 38 is adapted for executing the detection software 70.

The detection software 70 forms means for detecting particles 22 in the bodily fluid 24.

Alternatively, the detection means 70 are made as programmable logic components or further, or further as dedicated integrated circuits.

The detection software 70 is adapted for identifying, from the acquired images $I_n$, $I_{n+1}$, mobile elementary diffraction patterns 60, and for counting the moving particles 22 within the droplet 28, from the identified mobile elementary diffraction patterns.

In order to identify the mobile elementary diffraction patterns, the detection software 70 is for example adapted so as to detect on each acquired image $I_n$, at least one elementary diffraction pattern 60 corresponding to a particle 22 within the droplet 28, and then adapted tracking the position of each detected elementary diffraction pattern 60 of an acquired image $I_n$ at an instant $t_n$, to an image $I_{n+i}$ acquired at an instant $t_{n+i}$ i being an integer index generally comprised between 1 and 10. Preferably, the index i is equal to 1 and the time-dependent change of the position of each detected elementary pattern 60 between two consecutive images $I_n$ and $I_{n+1}$ is then detected.

By position tracking, is meant the tracking of the position of a point of the elementary diffraction pattern 60 between two images $I_n$ and $I_{n+i}$. This point may for example be a center 74 of the elementary diffraction pattern 60. Generally, a diffraction pattern is considered as a movement if between two acquired images $I_n$, $I_{n+i}$, the diffraction pattern moves along a distance greater than a predetermined minimum distance Dmin.

The predetermined minimum distance Dmin is for example greater than 5 pixels, or even than 10 pixels, for a time lap of the order of the one second, between the acquisition instants $t_n$, $t_{n+i}$.

Thus, the detection software 70 gives the possibility of detecting mobile elementary diffraction patterns 60, each of them corresponding to a particle moving in the liquid.

In order to identify the mobile elementary diffraction patterns, the detection software 70 is alternatively adapted for determining for each pixel, an image, a so called background image $I_{background}$, corresponding to an immobile component of a set of images $I_m$ to $I_{m+p}$, wherein m is a particular value of the index n, p is an integer greater than 1, generally comprised between 3 and 10, and for example equal to 5. The detection software 70 is then adapted for computing, for each acquired image $I_n$, a resulting image $I_n$ by subtracting for each pixel $I_n(x,y)$ of the acquired image the value of the pixel $I_{background}(x,y)$ from the determined background image $I_{background}$. Thus, $$I'_n(x,y)=I_n(x,y)-I_{background}(x,y) \quad (1)$$

The resulting image $I'_n$ then shows the mobile component of each of the images $I_n$ comprising the elementary diffraction patterns 60, and the detection software 70 is adapted for detecting, on each resulting image $I'_n$ one or several diffraction patterns, each detected diffraction pattern on the resulting image $I'_n$ corresponding to a mobile elementary diffraction pattern.

The background image $I_{background}$ is for example an image, a so called median image $I_{med}$, for which each pixel $I_{med}(x,y)$ has as a value the median value of the pixels $I_m(x,y), \ldots, I_{m+p}(x,y)$ of the set of images $I_m$ to $I_{m+p}$. In other words, $$I_{background}(x,y)=I_{med}(x,y)=\text{med}[I_m(x,y) \ldots I_{m+p}(x,y)] \quad (2)$$

wherein med designates the median operator.

The p images $I_m$ to $I_{m+p}$ may precede the image In. Alternatively, the image In may be part of the set of p images for which the background image $I_{background}$ is computed.

The background image $I_{background}$ then represents a reference image, on which the movements of the elementary diffraction patterns, visible in the images $I_m$ to $I_{m+p}$ are erased or attenuated. Thus, the background image $I_{background}$ may be considered as the image of a background common to each of the images $I_m$ to $I_{m+p}$, corresponding to the immobile component of each of these images.

Alternatively, the background image $I_{background}$ is obtained by calculating the average value of each pixel of the set of images $I_m$ to $I_{m+p}$. In other words:

$$I_{background}(x,y)=I_{mean}(x,y)=\text{mean}[I_m(x,y) \ldots I_{m+p}(x,y)] \quad (3)$$

wherein mean designates the mean operator, m is a particular value of the index n, p is an integer greater than 1, generally comprised between 3 and 10, and for example equal to 5.

Additionally, the thereby computed resulting image $I'_n$ is used for tracking the position of each detected elementary diffraction pattern 60. In other words, according to this optional addition, the detection software 70 is for example adapted for detecting the diffraction patterns, tracking the position of the diffraction patterns and counting the particles 22 moving in the droplet 28 according to the mobile elementary diffraction patterns, from resulting images $I'_n$ instead and in the place of the acquired images $I_n$, with the index n varying between 1 and N.

Thus, it is possible to identify the mobile elementary diffraction patterns 60 between two images $I_n$, $I_{n+i}$. Their counting gives the possibility of estimating the number of moving particles in the liquid 24.

An important aspect of the invention is therefore the discrimination between the immobile elementary patterns and the mobile elementary diffraction patterns, the latter being counted for estimating the number of particles in the liquid.

When the liquid 24 to be analyzed appears as a droplet 28, the convection currents allow displacement of the particles 22 in the droplet. The detection of these particles, and their counting, gives the possibility of avoiding detection of parasitic elements not present in the droplet 28, but may generate elementary diffraction patterns on the photodetector and therefore distort the measurement. Such elements are for example dusts, or even scratches, present on the transparent support 26, on the confinement element 46 or at the surface of the photodetector 32. By exclusively counting the moving particles 22, taking into account of the immobile elements is avoided, which generate fixed elementary diffraction patterns, i.e. immobile, unlike the moving particles in the droplet.

Let us specify that the increase in the temperature of the droplet 28 gives the possibility of amplifying the convection currents within the droplet 28, which increases the mobility of the particles 22 present in the latter. Because of the proximity between the droplet 28 and the photodetector 32, the temperature of the droplet 28 tends to increase to a temperature comprised between 40° Celsius and 50° Celsius, then promoting movement of the particles 22.

Also, generally, it is preferable that the liquid to be analyzed 24 be mobile, and in particular deposited as a droplet 28, deposited on the transparent substrate 26 and exposed to open air: this allows spontaneous movement of the particles 22 in the droplet 28. The fact of positioning the bodily fluid 24 as a droplet 28 includes many advantages:

a volume of the order of a few µl to a few tens of µl, sufficiently large for obtaining a reliable diagnostic, spontaneous setting into motion of the particles 22 to be detected, simplicity in the application, a simple deposit being sufficient, compatibility with observation by lens-less imaging, the field depth may attain several centimeters: all the particles 22 present in the droplet produce an elementary diffraction pattern 60 which may be utilized.

Optionally and additionally, the detection software 70 is adapted for characterizing the identified mobile elementary diffraction patterns. The term of <<characterizing>> designates the determination of a quantitative parameter relative to an elementary diffraction pattern. An example of such a parameter will be described subsequently.

Optionally and additionally, the detection software 70 is also adapted for sorting the detected elementary diffraction patterns 60 according to at least two distinct categories, for classifying the particles 22 corresponding to the detected elementary diffraction patterns 60 according to at least two distinct classes, each class being associated with a respective category. The sorting, also called classification, is carried out according to a parameter determined during the characterization phase of the particles.

Figure 6:
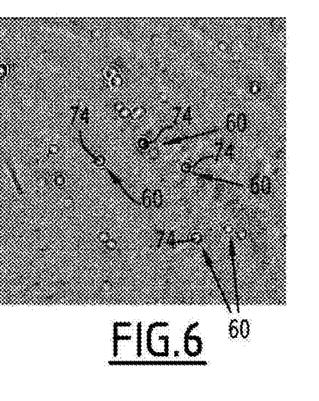
FIG. 6 is an enlargement of the framed area VI of FIG. 5.

In order to notably track the position of the diffraction patterns, the detection software 70 is adapted for localizing, in the acquired image $I_n$ or in the resulting image $I'_n$, a particular point, for example the center 74, of each elementary diffraction pattern 60, as illustrated in FIGS. 4 and 6. The localization of each particular point, such as the center 74, is for example carried out by applying an autocorrelation function, preferably normalized, so as to obtain from the observed image $I_n$ and from a reference elementary diffraction pattern $I_R$, a correlation image de $I_C$, satisfying the following equation:

$$I_C(x, y) = \frac{\sum_{i,j} I_R(i, j) \times I_n(x+i, y+j)}{\sqrt{\sum_{i,j} I_R(i, j)^2 \times \sum_{i,j} I_n(x+i, y+j)^2}} \quad (4)$$

On the correlation image $I_C$, each intensity peak then corresponding to the position of the center 74 of the diffraction pattern corresponding to the reference image $I_R$.

The reference elementary diffraction pattern $I_R$ is established beforehand on the basis of modeling or on the basis of experimental images.

Alternatively, for detecting the center 74 of the diffraction pattern, the detection software 70 is adapted for reconstructing an image of the diffracting particles 22 from the acquired image $I_n$ or from the resulting image $I'_n$, and according to a known holographic reconstruction algorithm. Such an algorithm gives the possibility from an elementary diffraction pattern, of reconstructing the geometry and/or the position of the diffracting object. The detection software 70 is then able to detect in the reconstructed image the position corresponding to the center 74 of each diffraction pattern, and then of determining a region of the acquired image $I_n$ or resulting image $I'_n$, this region including the corresponding elementary diffraction pattern 60. The detection software 70 is finally able to detect the center 74 of the diffraction pattern by matching with the detected position in the reconstructed image. The application of such an algorithm however requires control of the geometry of the liquid. It notably applies when a liquid filling a fluidic chamber is analyzed, the liquid being set into motion in said chamber.

Alternatively, the determination of the center 74 of an elementary diffraction pattern 60 is carried out manually, the operator carrying out a manual selection of the area of the image considered as representative of the central area of a corresponding elementary diffraction pattern 60.

Figure 9:
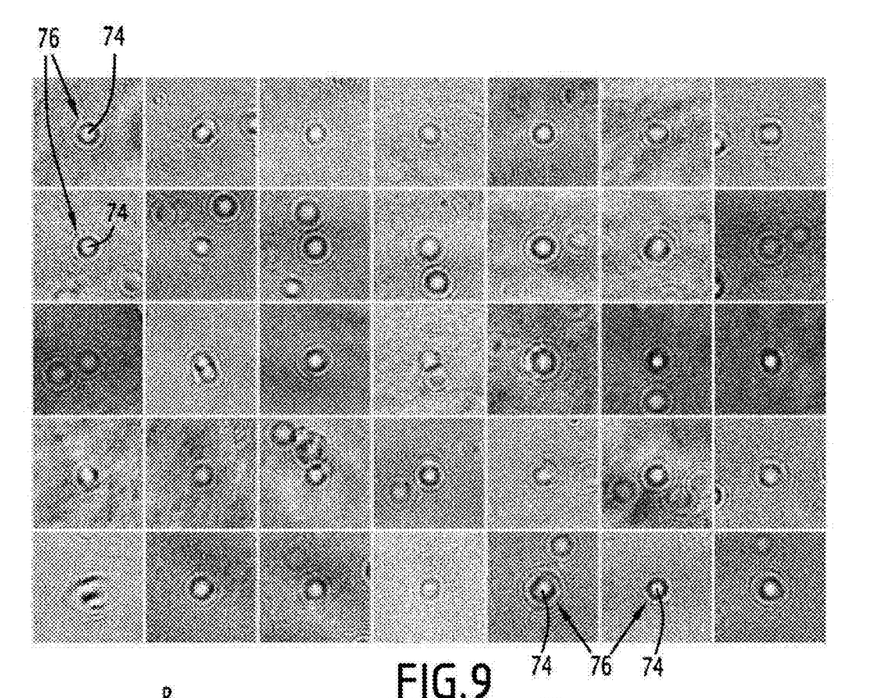
FIG. 9 is a set of views obtained with the photodetector of FIG. 2 for a same sample of cerebrospinal liquid, each containing a diffraction pattern corresponding to a respective white corpuscle.
Figure 10:
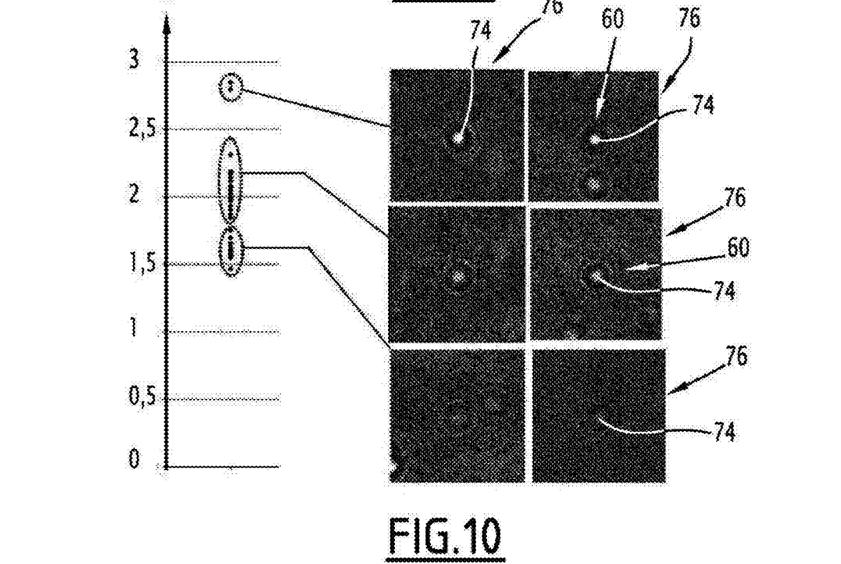
FIG. 10 is a set of points each representing a ratio between the maximum intensity and the median intensity of a region of interest of from a respective view of FIG. 9 including a corresponding diffraction pattern.

From the coordinates, in the image $I_n$, of the center 74 of each thereby identified elementary diffraction pattern, a region of interest 76 around this center 74 as illustrated in FIGS. 9 and 10 is for example defined. The region of interest 76 typically comprises from 10 to 1,000 pixels, preferably from 10 to 100 pixels.

The detection software 70 is adapted for carrying out a tracking of the position of each detected elementary diffraction pattern 60 of an acquired image $I_n$ to the next acquired image $I_{n+1}$, or respectively of a resulting image $I'_n$ to the next resulting image $I'_{n+1}$, with a cell tracking method which for example consists of pairing in two successive images $I_n$, $I_{n+1}$, $I'_{n+1}$, the closest particles. Such a method for tracking cells is for example described in the article <<Automated tracking of migrating cells in phase-contrast video microscopy sequences using image registration>> of Hand A. J.; Sun T.; Barber D. C.; Hose D. R, MacNeil S., published in the journal: Journal of Microscopy in 2009, volume 234, pages 62 to 79.

The detection software 70 is then adapted for determining, from among the tracked elementary diffraction patterns 60, the mobile diffraction patterns for which the displacement between two successive acquired images $I_n$, $I_{n+1}$, respectively between two successive resulting images $I'_{n+1}$, is greater than the predetermined minimum distance $D_{min}$, the particles corresponding to these mobile elementary diffraction patterns 60 being then considered as moving particles within the droplet 28. The detection software 70 is further adapted for counting the moving particles within the droplet 28, i.e. the one for which the displacement of the corresponding diffraction patterns is greater than the predetermined minimum distance $D_{min}$.

Figure 11:
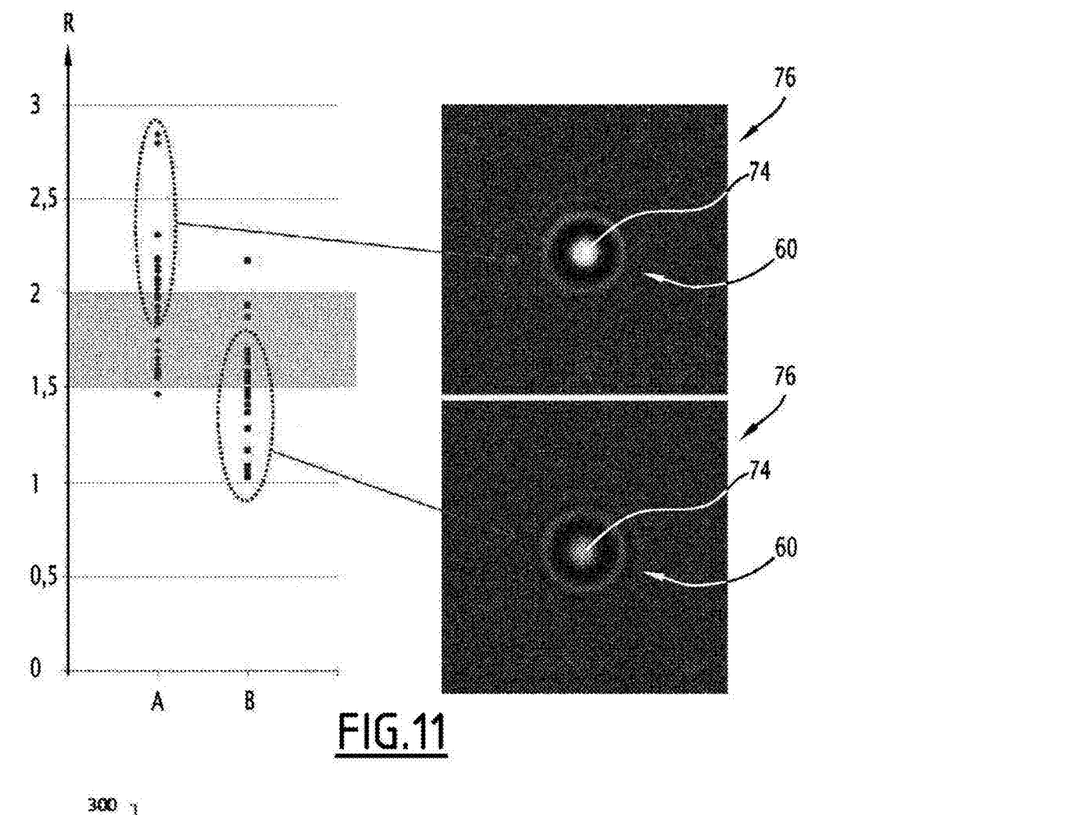
FIG. 11 is a view similar to that of FIG. 10, with several samples of cerebrospinal liquid of different patients.

The detection software 70 is, as an optional addition, adapted for characterizing each identified mobile elementary diffraction pattern 60, i.e. determining one or several criteria for each of these patterns. Such a criteria is for example a ratio R between the maximum intensity and the median intensity (or the mean intensity) of the region of interest 76 of said diffraction pattern. Examples of the value of the ratio R for the different diffraction patterns 60, each associated with a corresponding region of interest 76, are illustrated in FIGS. 10 and 11.

The detection software 70 is then able to sought out the detected elementary diffraction patterns 60 according to at least two distinct categories according to the selected characterization criterion, in order to classify the particles corresponding to the detected elementary diffraction patterns according to distinct classes.

The classification of said diffraction pattern 60 is then carried out by comparing the computed ratio R with at least one predetermined threshold. In other words, according to this example, a criterion for classifying the patterns is a comparison relationship of the computed ratio R with one or several corresponding predetermined thresholds.

Figure 3:
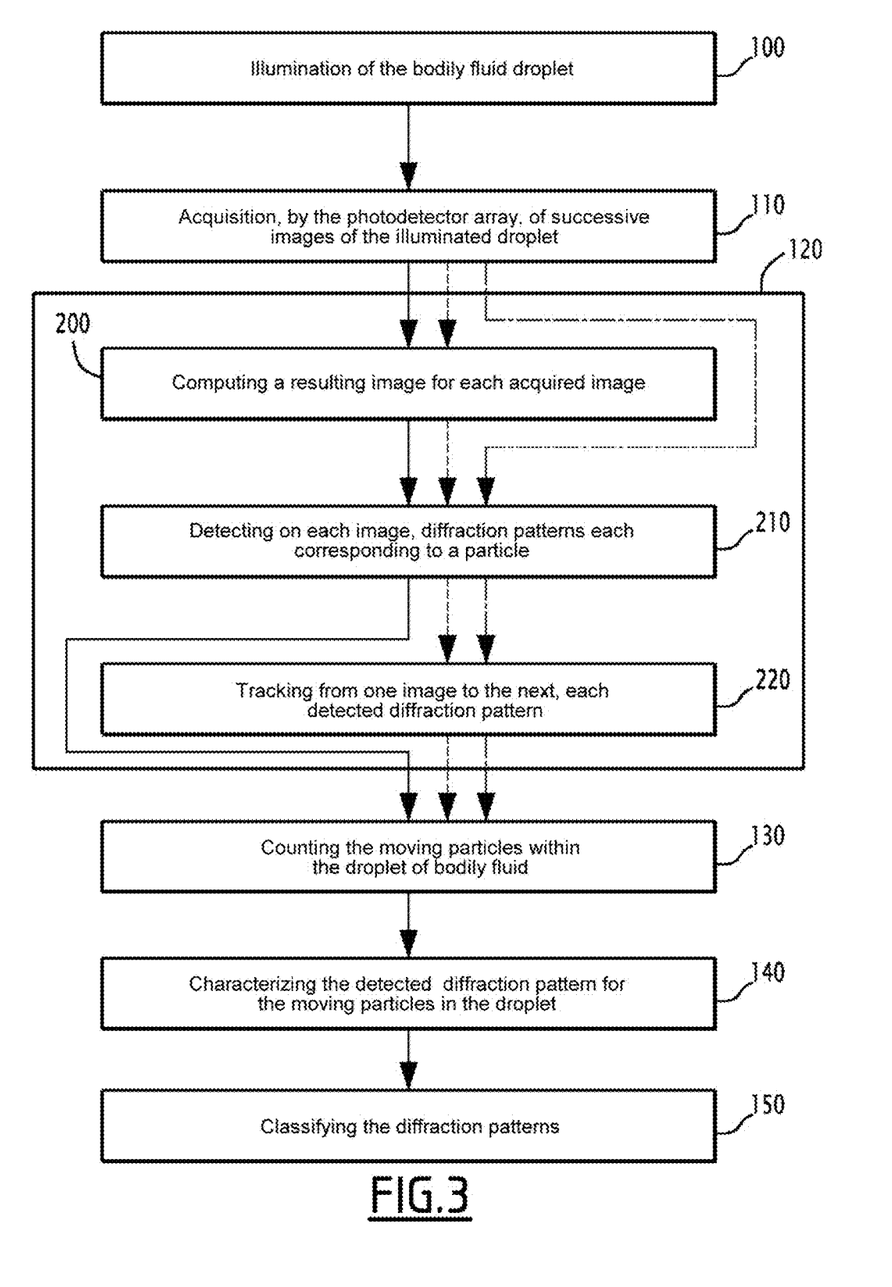
FIG. 3 is a flowchart of a detection method according to the invention.

The operation of the detection system 20 according to the invention will now be described with the FIG. 3 illustrating a flow chart of the detection method according to the invention.

During the initial step 100, the bodily fluid 24 is deposited as a droplet 28 on the transparent substrate 26, in particular on the transparent slide 48. In the described example, and in order to diagnose meningitis, the bodily fluid 24 is cerebrospinal liquid, and the amount of bodily fluid deposited on the transparent substrate 26, as a droplet 28, is for example equal to 10 μm. The transparent slide 48 is itself laid at the bottom of the Petri dish 46 in order to control the spreading out of the droplet 28 on the slide 48. The droplet 28 of bodily fluid is then illuminated with the spatially coherent light source 30, the light beam 50 being directed along the vertical direction Z.

During step 110, the photodetector array 32 carries out the sequential acquisition of several transmission images $I_n$, $I_{n+1}$ at successive instants $t_n$, $t_{n+1}$. Each transmission image $I_n$, $I_{n+1}$ is formed by the transmitted radiation corresponding to the acquisition instant $t_n$, $t_{n+1}$, by the illuminated bodily fluid 24. In other words, the photodetector array 32 produces images of the elementary diffraction patterns 60 transmitted by the particles found in the illuminated bodily fluid 24, each elementary diffraction pattern corresponding to waves diffracted by the diffracting particles 22 during the illumination of the liquid 24, these diffracted waves interfering with the incident light wave.

The number of acquired images $I_n$ is for example equal to 10, and the number N is then equal to 10.

The observation of a diffraction pattern which may be utilized, by placing the photodetector array 32 at a relatively small distance is notably due to the absence of magnification optics between the bodily fluid 24 and the photodetector array 32.

During the acquisition step 110, the photodetector 32 is preferably positioned at a small distance from the bodily fluid 24, the second distance D2 between the bodily fluid 24 and the photodetector 32 along the vertical direction Z for example being of the order of a few millimeters, and preferably less than 1 cm.

At the end of the acquisition step 110, the detection software 70 carries out, during step 120 the identification, from the acquired images $I_n$, $I_{n+1}$, of the mobile elementary diffraction patterns 60. This step 120 for identifying the mobile diffraction patterns will be described in more detail later on.

During the next step 130, the detection software 70 performs counting of the moving particles 22 within the droplet 28, from the thereby identified mobile elementary diffraction patterns.

Optionally and additionally, the detection software 70 may apply, during step 140, the characterization of the detected elementary diffraction patterns corresponding to the moving particles according to at least two distinct categories, in order to classify, during step 150, the moving particles associated with these detected elementary diffraction patterns. The characterization step 140 will be described in more detail subsequently.

In order to identify the mobile diffraction patterns mobiles during step 120, three methods will now be described.

According to a first method, illustrated in FIG. 3 by the solid line path inside step 120, the detection software 70 determines during a sub-step 200, for each pixel (x,y), a median value or alternatively a mean value, of the intensity of said pixel for a set of acquired images $I_m$ to $I_{m+p}$, and preferably for the whole of the acquired images, i.e. the images $I_n$ with n being comprised between 1 and N. The background image $I_{background}$ is defined beforehand according to equation (2), or alternatively according to equation (3).

Le detection software 70 then computes, always during this substep 200, for each acquired image of said set, preferably for each of the acquired images, the resulting image $I'_n$ by substraction according to the preceding equations (1) and (2), from the measured value of the intensity of each pixel of the acquired image $I_n$, of the previously determined median value, or alternatively of the average value according to the preceding equations (1) and (3).

Figure 5:
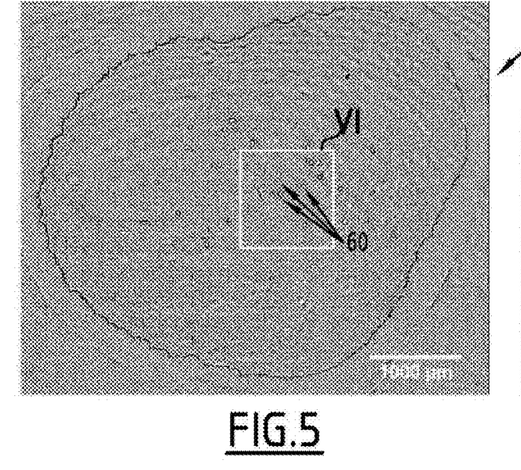
FIG. 5 is a view of a resulting image obtained from the acquired image of FIG. 4 and by subtracting from the value of the intensity of each pixel of the acquired image, a median intensity value of said pixel, the median value being determined for a set of acquired images.

The computation of these resulting images $I'_n$ by substraction of the median value, or alternatively the mean value, from each of the pixels, gives the possibility of viewing the mobile elementary diffraction patterns, the so-called immobile component of the image $I_n$ being removed, or at least attenuated. These mobile diffraction patterns correspond to the moving particles 22 in the droplet 28. In other words, the resulting images $I'_n$ give the possibility of identifying the moving particles in the droplet 28. This is moreover clearly visible by comparing FIG. 4 corresponding to an acquired image $I_n$, with FIGS. 5 and 6 corresponding to the resulting image $I'_n$ associated with the acquired image of FIG. 4. In FIG. 5, only the mobile particles of FIG. 4 appear. Moreover it is noticed that the sole diffraction patterns visible in FIG. 5 are located inside an area corresponding to the droplet 28 (the outer periphery of the droplet 28 being in the shape of a quite wide peripheral border on FIGS. 4 and 5), while, in FIG. 4 corresponding to the acquired image, diffraction patterns are visible both inside the area corresponding to the droplet 28 and outside of this area corresponding to the droplet 28.

After sub-step 200, the detection software 70 detects, during the sub-step 210, on each resulting image $I'_n$, each elementary diffraction pattern 60 corresponding to a particle 22 within the droplet 28. For this purpose, the detection software 70 carries out for example as described earlier, a comparison between the resulting image and a reference diffraction pattern by autocorrelation, preferably normalized autocorrelation, between said image and the reference diffraction pattern, each intensity peak in the obtained autocorrelation image corresponding to the position of the center 74 of a corresponding diffraction pattern.

Alternatively, as described earlier, the localization in the image of the center 74 of each elementary diffraction pattern 60 is achieved with a reconstruction of an image of the particle 22 associated with the corresponding elementary diffraction pattern 60 by applying a known reconstruction algorithm, and then from the detection, in the reconstructed image, of the position corresponding to the center of said elementary diffraction pattern 60.

Further alternatively, the detection of the center 74 of each elementary diffraction pattern 60 is achieved manually by the operator, the latter making a manual selection of the area of the relevant image as representative of the central area of the diffraction pattern.

Further, alternatively, the center 74 of each elementary diffraction pattern 60 is obtained by grey level thresholding operations, and then with Boolean operations applied to the thresholded image.

Once the diffraction patterns are detected, each corresponding to a moving particle 22 in the droplet 28, the detection software 70 then counts the moving particles within the droplet 28 of bodily fluid, during step 130 which follows the sub-step 210 according to the first method for identifying mobile diffraction patterns.

According to a second identification method, illustrated in FIG. 3 by the path in dotted lines inside step 120, the detection software 70 still computes during the sub-step 200 the resulting image I'$_n$ of each acquired image I$_n$, and then detects during the sub-step 210 the diffraction patterns in the resulting image I'$_n$.

According to the second method, the detection software 70 additionally carries out, during a sub-step 220, the tracking of a resulting image I'$_n$ to the next resulting image I'$_{n+1}$ of each detected diffraction pattern. This sub-step is carried out by applying a tracking algorithm, as described earlier, such as the algorithm described in the aforementioned article of Hand et al.

This second method then allows even more reliable identification of the mobile diffraction patterns corresponding to the moving particles in the droplet 28.

During step 130 which follows the sub-step 220 according to this second identification method, the detection software 70 then counts the moving particles within the droplet 28 of bodily fluid, i.e. the particles 22 for which the corresponding elementary diffraction patterns 60 have achieved a displacement greater than the predetermined minimum distance D$_{min}$ between two successive acquisitions corresponding to the instants t$_n$, t$_{n+1}$. The displacement of each elementary diffraction pattern 60 from a resulting image I'$_n$ to the other one I'$_{n+1}$ is preferably computed by measuring the displacement of the center 74 of said pattern from one image I'$_n$ to the other I'$_{n+1}$.

The fact of counting the moving particles within the droplet 28 by further achieving tracking of the diffraction patterns from resulting images I'$_n$, I'$_{n+1}$ allows determination with more accuracy of the number of moving particles in the droplet 28.

According to a third identification method, illustrated in FIG. 3 by the path in dashed lines inside step 120, the computation of the resulting image is not carried out, and the method directly passes from step 110 to the sub-step 210 during which the detection software 70 detects, on each acquired image I$_n$ with n varying between 1 and N, each elementary diffraction pattern 60 corresponding to a particle 22 within the droplet 28. This detection is carried out in an identical way with what has been described earlier for detecting diffraction patterns in each resulting image I'$_n$, except that, according to this third identification method, the detection is carried out here in each acquired image I$_n$.

Figure 7:
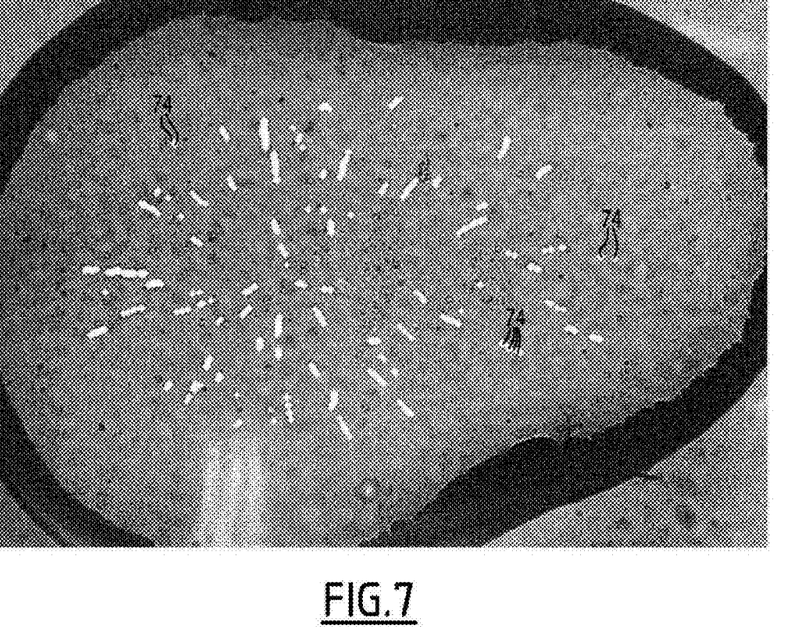
FIG. 7 is an image illustrating a tracking of the diffraction patterns, the white points corresponding to the successive positions of centers of said diffraction patterns.

According to this third identification method, the detection software 70 then carries out, during the next sub-step 220, the tracking of an acquired image I$_n$, to the next acquired image I$_{n+1}$, of each detected diffraction pattern. This sub-step is carried out by applying the cell tracking algorithm, as described earlier, such as the algorithm described in the aforementioned article of Hand et al. The tracking of the diffraction patterns 60 in the acquired images I$_n$ is illustrated in FIG. 7 wherein the white points correspond to the successive positions of the centers 74 of said diffraction patterns.

During step 130 which follows the sub-step 220 according to this third identification method, the detection software 70 then counts the moving particles within the droplet 28 of bodily fluid, i.e. the particles 22 for which the corresponding elementary diffraction patterns 60 have performed a displacement greater than the predetermined minimum distance D$_{min}$ between two successive acquisitions corresponding to the instants t$_n$, t$_{n+1}$.

This third identification method then allows identification of the mobile diffraction patterns directly in the acquired images, without having to compute the background image I$_{background}$, while obtaining sufficiently reliable results for detecting as early as possible a possible disease, for example diagnosing cases of meningitis.

The method for detecting particles according to the invention, and for counting the moving particles within the droplet 28, allows for example determination of the number of white corpuscles in a predetermined amount of cerebrospinal fluid, the bodily fluid 24 being the cerebrospinal fluid and the detected particles 22 being the white corpuscles contained in said cerebrospinal fluid.

The determination of the number of white corpuscles in a predetermined amount of cerebrospinal fluid may then carry out a diagnostic of meningitis, since it is generally considered that meningitis is diagnosed if the number of white corpuscles present in a predetermined amount of cerebrospinal fluid is greater than a predetermined threshold value. The predetermined threshold value is for example equal to 10 when the predetermined amount of cerebrospinal fluid is substantially equal to 10 µL.

Additionally, during the step 110 for acquiring successive images of the illuminated droplet 28, the droplet 28 is further heated in order to promote displacement of the particles 22 within the droplet 28. The heating of the droplet 28 is for example applied with the photodetector array 32, the latter forming a heat source. In the example of FIG. 1, the heating of the droplet 28 is for example obtained by reducing the cooling performed by the heat dissipater 42 and the fan 44, in order to cause slight heating of the photodetector array 32, and then of the droplet 28 located in proximity to said photodetector 32. The heating of the droplet 28 is for example of the order of a few degrees Celsius with respect to the room temperature, the temperature of the droplet 28 for example being comprised between 40° C. and 50° C.

Figure 8:
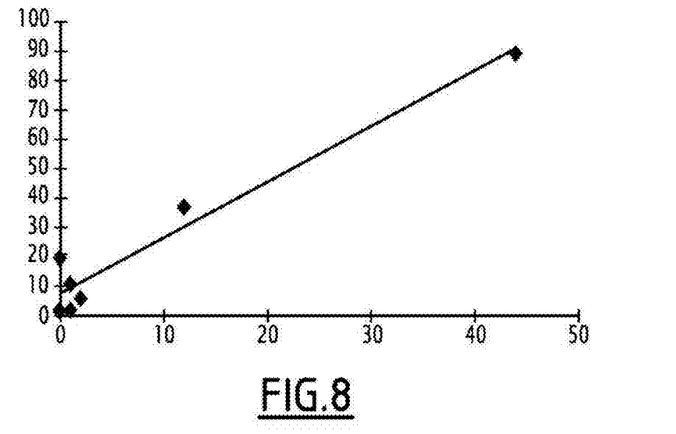
FIG. 8 is a set of points illustrating the number of white corpuscles detected in the droplet of cerebrospinal liquid, with in abscissas the number of white corpuscles determined with a cytometry method and in ordinates that determined with the detection system and method according to the invention, each point corresponding to a sample of cerebrospinal liquid of a respective patient.

FIG. 8 then shows that the results obtained with the detection method according to the invention are consistent with the results obtained via a reference method for counting particles, in this case cytometry. The detection method according to the invention allows efficient identification of the bodily fluid samples 24 including a significant amount of moving particles with respect to the bodily fluid samples 24 including very little moving particles 22.

In the example of FIG. 8, the bodily fluid 24 is cerebrospinal fluid and the detected moving particles 22 are white corpuscles. For each sample of cerebrospinal fluid illustrated by a lozenge, the number in abscissas corresponds to the number of determined white corpuscles according to the reference method by cytometry and the number in ordinates corresponds to the number of determined white corpuscles with the detection method according to the invention. For a first sample of cerebrospinal fluid corresponding to the right most lozenge in FIG. 8 (sample 1 of the table hereafter), the determined number of white corpuscles via the detection method according to the invention is equal to 89 and the determined number of white corpuscles for this same sample with a cytometry method is equal to 44. For a second sample corresponding to the lozenge located in the middle of FIG. 8 (sample 7 of the table hereafter), the determined number of white corpuscles with the detection method according to the invention is equal to 37, and the one determined by cytometry for this same sample is equal to 12. For the other samples of cerebrospinal fluid (samples 2 to 6 of the table hereafter), corresponding to the lozenges located on the left of FIG. 8, the determined number of white corpuscles is small, for example less than or equal to 10, whether this is with the method according to the invention or by cytometry, and corresponds to absence of meningitis.

The results of the number of determined white corpuscles with the detection method according to the invention and according to the cytometry method are further indicated in the table hereafter for each tested sample of bodily fluid 24.

TABLE 1

| Sample number | Number of white corpuscles by cytometry | Number of white corpuscles with the method according to the invention |
|---|---|---|
| 1 | 44 | 89 |
| 2 | 1 | 2 |
| 3 | 0 | 2 |
| 4 | 2 | 6 |
| 5 | 0 | 20 |
| 6 | 1 | 11 |
| 7 | 12 | 37 |

Even if the detected number of moving particles with the method according to the invention is relatively different from the detected number of particles by cytometry in the droplet 28 of bodily fluid, the detection method according to the invention nevertheless gives the possibility of discriminating a bodily fluid 24 including a large number of particles in motion from a bodily fluid 24 including few moving particles, so that a diagnostic associated with the sampled bodily fluid 24, such as diagnostic of meningitis, remain satisfactory as illustrated in FIG. 8. Naturally, this method is still to be refined, but as of now it is possible to assert that when the number of particles exceeds a certain threshold, such as a threshold of 20 white corpuscles in a volume of 10 µL, complementary analysis by a reference method is recommended. Thus, this method, simple to apply, fast and inexpensive, is an efficient aide to diagnosing.

The characterization step 140 is for example carried out with the computation of the ratio R between the maximum intensity and the median intensity of the region of interest 76 of the image including said diffraction pattern. Such a characterization is illustrated in FIGS. 10 and 11 for which the bodily fluid 24 is cerebrospinal fluid, and the particles to be classified are corpuscles, to be classified according to two distinct classes, i.e. white corpuscles and red corpuscles.

In FIG. 11, column A corresponds to white corpuscles and the values of the ratio R, associated with the column A in ordinates and computed for the different diffraction patterns corresponding to the white corpuscles, are comprised between about 1.5 and 2.8. More specifically, the values of the ratio R are most frequently greater than 1.75 when the diffraction patterns correspond to white corpuscles. This is confirmed by FIGS. 9 and 10, FIG. 9 showing the 35 diffraction patterns obtained on the sample from a patient affected with meningitis, a sample which only contains white corpuscles according to a cytometry measurement carried out in parallel. FIG. 10 illustrates the e values of the ratio R computed for each of the 35 diffraction patterns, the values of the ratio R being spread out from 1.5 to 2.8, mainly from 1.75 to 2.8.

In FIG. 11, column B corresponds to red corpuscles, and the values of the ratio R, associated with column B in ordinates, are comprised between 1 and 2.25, and generally less than 1.75.

In other words, with a predetermined threshold equal to 1.75 in the example of FIG. 11, the computation of the ratio R will allow quite efficient discrimination between the red corpuscles and the white corpuscles, the white corpuscles being considered as moving particles for which the associated ratio R is greater than the predetermined threshold, selected to be equal to 1.75, and the red corpuscles being considered as moving particles for which the associated ratio R is less than the predetermined threshold.

Thus, the method may comprise a step 150 for classifying the detected particles, depending on the established characterization criterion, for each of them, during the characterization phase.

Figure 12:
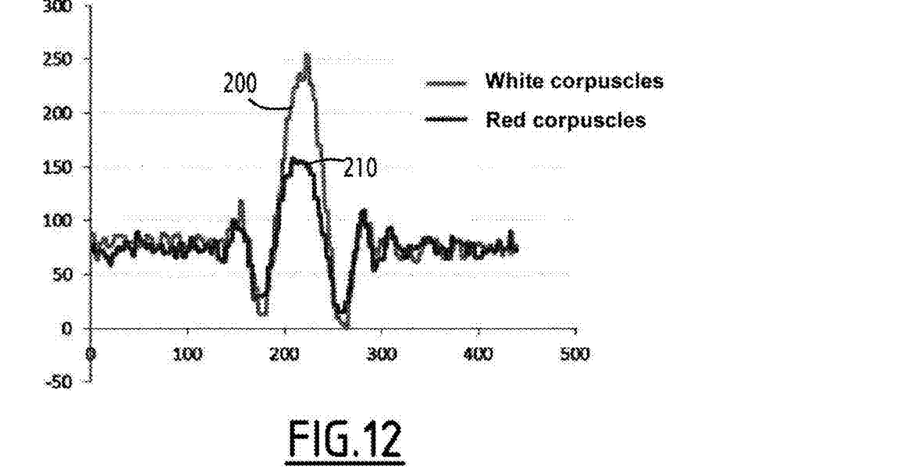
FIG. 12 is a set of two curves, one for a white corpuscle and the other for a red corpuscle, each curve illustrating an intensity profile in the vicinity of the center of the diffraction pattern versus a distance expressed in µm, the center of the diffraction pattern corresponds to the distance equal to 225 µm.

This difference in ratio R between white corpuscles and red corpuscles is also visible in FIG. 12 wherein the curve 200 represents an intensity profile in the vicinity of the center 74 of the diffraction pattern associated with a while corpuscle, depending on a distance expressed in µm, the center 74 of the diffraction pattern corresponding to the distance substantially equal to 225 µm. Curve 210 similarly illustrates an intensity profile in the vicinity of the center 74 of the diffraction pattern corresponding to a red corpuscle, depending on the distance expressed in µm, the center 74 also corresponding to the distance substantially equal to 225 µm.

It is then ascertained that the maximum intensity of the diffraction pattern associated with the white corpuscle is greater than the one associated with the red corpuscle, while the median intensity of the diffraction pattern is substantially equal for the white corpuscle and for the red corpuscle, so that the ratio R is higher with the white corpuscle than with the red corpuscle.

The classification achieved during step 150 between two types of particles, such as for example between the white corpuscles and the red corpuscles, then gives the possibility of distinguishing between two forms of meningitises, i.e. infectious meningitis and meningeal hemorrhage. Indeed, infectious meningitis corresponds to the case when the moving particles are white corpuscles, and meningeal hemorrhage corresponds to that when the moving particles are red corpuscles.

It is thus conceivable that the detection method and system 20 according to the invention allow detection of the moving particles 22 in the bodily fluid 24 in a particularly inexpensive way and easy to apply. This then gives the possibility of carrying out continuous counting of the detected particles, and of diagnosing if required a particular disease, such as meningitis.

The invention claimed is:

1. A method for detecting at least one particle in a bodily fluid, with a detection system comprising a light source, a transparent substrate and a photodetector array, the transparent substrate being positioned between the light source and the photodetector array,
   the method comprising:
      placing the bodily fluid as a droplet on the transparent substrate,
      illuminating the droplet with the light source,
      acquiring several successive images of the droplet with the photodetector array, each image being formed by radiation transmitted through the illuminated droplet and including at least one elementary diffraction pattern, each elementary diffraction pattern corresponding to waves diffracted by a particle during the illumination of the droplet,
      identifying, from the acquired images, mobile elementary diffraction patterns,
      counting moving particles within the droplet, from the thereby identified mobile elementary diffraction patterns.

2. The method according to claim 1, wherein the method further comprises heating the droplet for promoting displacement of particles within the droplet.

3. The method according to claim 1, wherein each acquired image includes a plurality of pixels and the photodetector array is adapted for measuring the intensity of each pixel, and
wherein identifying the mobile elementary diffraction patterns includes:
the determination, for each pixel of the image, of the median value or of the mean value of the intensity of said pixel for a set of acquired images,
the computation for at least one acquired image, of a resulting image by subtracting, for each pixel of the acquired image, said median value or said mean value, and
the detection, on each resulting image, of at least one diffraction pattern, each detected diffraction pattern on the resulting image corresponding to a mobile elementary diffraction pattern.

4. The method according to claim 3, wherein the identification further includes the tracking of each detected elementary diffraction pattern of a resulting image to the next resulting image, each mobile elementary diffraction pattern having between two successive resulting images, a displacement greater than a predetermined minimum distance.

5. The method according to claim 1, wherein identifying the mobile elementary diffraction patterns includes:
the detection, on each acquired image, of at least one elementary diffraction pattern corresponding to a particle within the droplet, and
the tracking of each detected elementary diffraction pattern of an acquired image to the next acquired image, each mobile elementary diffraction pattern having, between two successive acquired images, a displacement greater than a predetermined minimum distance.

6. The method according to claim 1, wherein the method further comprises characterizing the detected moving elementary diffraction patterns and classifying the characterized patterns according to at least two distinct categories.

7. The method according to claim 6, wherein the characterization includes the computation, for each identified mobile elementary diffraction pattern, of a ratio between the maximum intensity and the median intensity of a region of interest of the image including said identified mobile elementary diffraction pattern, the classification of said diffraction pattern then being carried out depending on the computed value of the ratio.

8. The method according to claim 3, wherein the detection includes the localization in the image of the center of each elementary diffraction pattern.

9. The method according to claim 8, wherein the localization in the image of the center of each elementary diffraction pattern is achieved via autocorrelation with a reference elementary diffraction pattern.

10. The method according to claim 8, wherein the localization in the image of the center of each elementary diffraction pattern is achieved from:
reconstruction of an image of the particle associated with said elementary diffraction pattern, by applying a reconstruction algorithm, and then
detecting, in the reconstructed image, the position corresponding to the center of said elementary diffraction pattern.

11. A method for diagnosing meningitis, comprising the following steps:
determining a number of white corpuscles in a predetermined amount of cerebrospinal fluid with a detection method according to claim 1, the bodily fluid being the cerebrospinal fluid and the detected particles being the white corpuscles contained in said cerebrospinal liquid,
diagnosing meningitis if the number of detected white corpuscles in the predetermined amount of cerebrospinal fluid is greater than a predetermined threshold value.

12. A system for detecting at least one particle in a bodily fluid, the system comprising:
a transparent substrate adapted for receiving the bodily fluid as a droplet,
a light source adapted for emitting a light beam for illuminating the droplet,
a photodetector array adapted for acquiring several successive images of the droplet, each image being formed by radiation transmitted through the illuminated droplet and including at least one elementary diffraction pattern, each elementary diffraction pattern corresponding to waves diffracted by a particle upon illumination of the droplet, and
an information processing unit adapted for:
identifying, from the acquired images, mobile elementary diffraction patterns,
counting moving particles within the droplet, from the identified mobile elementary diffraction patterns.

* * * * *